(12) United States Patent
Estes

(10) Patent No.: US 8,465,492 B2
(45) Date of Patent: Jun. 18, 2013

(54) CHUCK FOR RECIPROCATING SURGICAL INSTRUMENT

(75) Inventor: Larry D. Estes, North Richland Hills, TX (US)

(73) Assignee: Medtronic Xomed, Inc., Jacksonville, FL (US)

( * ) Notice: Subject to any disclaimer, the term of this patent is extended or adjusted under 35 U.S.C. 154(b) by 1227 days.

(21) Appl. No.: 12/165,305

(22) Filed: Jun. 30, 2008

(65) Prior Publication Data
US 2009/0326540 A1  Dec. 31, 2009

(51) Int. Cl.
*A61B 17/00* (2006.01)
*B23B 31/16* (2006.01)
*B23B 31/12* (2006.01)
*B25G 3/02* (2006.01)

(52) U.S. Cl.
USPC ............................ 606/82; 279/71; 279/81

(58) Field of Classification Search
USPC ................... 279/71, 81, 146; 606/82
See application file for complete search history.

(56) References Cited

U.S. PATENT DOCUMENTS

| | | | |
|---|---|---|---|
| 2,935,329 A * | 5/1960 | Hessler ...................... | 279/51 |
| 4,020,555 A | 5/1977 | Hedrick | |
| 4,985,031 A | 1/1991 | Buss et al. | |
| 5,035,698 A | 7/1991 | Comparetto | |
| 5,505,737 A | 4/1996 | Gosselin et al. | |
| 5,569,256 A | 10/1996 | Vaughn et al. | |
| 5,609,603 A | 3/1997 | Linden | |
| 5,658,304 A | 8/1997 | Lim | |
| 5,676,680 A | 10/1997 | Lim | |
| 5,729,904 A | 3/1998 | Trott | |
| 5,741,263 A | 4/1998 | Umber et al. | |
| 5,782,836 A | 7/1998 | Umber et al. | |
| 5,839,196 A | 11/1998 | Trott | |
| 5,846,244 A | 12/1998 | Cripe | |
| 5,893,851 A | 4/1999 | Umber et al. | |

(Continued)

FOREIGN PATENT DOCUMENTS

| | | |
|---|---|---|
| AU | 2009265082 A1 | 1/2010 |
| CA | 2729454 A1 | 1/2010 |

(Continued)

OTHER PUBLICATIONS

"PneuMicro Small Bone Power System," printed from www.brasselerusamedical.com/sbChanges/OpsManual.pdf on Jun. 23, 2008, pp. 1-16.

(Continued)

*Primary Examiner* — Kevin T Truong
*Assistant Examiner* — David Bates
(74) *Attorney, Agent, or Firm* — Harness, Dickey

(57) ABSTRACT

Devices are described relating to the retaining of surgical tools within the chuck of a reciprocating surgical instrument, such as a reciprocating saw. A securing chuck is disclosed for securing a surgical tool to a reciprocating surgical instrument that comprises a shaft and a securing member. The shaft defines an axis and has a cylindrical bore extending along the axis. The bore is shaped to receive a substantially rounded tool shank. A pair of transverse slots extends into the shaft along a plane passing through the axis for receiving a substantially flattened tool shank. The transverse slots intersect with the cylindrical bore. The securing member is carried by the shaft and is radially movable relative to the bore both inwardly and outwardly to secure the surgical tool in the chuck.

18 Claims, 10 Drawing Sheets

U.S. PATENT DOCUMENTS

| | | | |
|---|---|---|---|
| 6,007,541 A | 12/1999 | Scott | |
| 6,045,564 A | 4/2000 | Walen | |
| 6,209,208 B1 * | 4/2001 | Marinkovich et al. | 30/392 |
| 6,344,043 B1 | 2/2002 | Pappas | |
| 6,725,548 B1 | 4/2004 | Kramer et al. | |
| 6,860,886 B1 | 3/2005 | Lee | |
| 8,272,135 B2 | 9/2012 | Zhou | |
| 2003/0023256 A1 | 1/2003 | Estes et al. | |
| 2003/0055432 A1 | 3/2003 | Steiger | |
| 2004/0194324 A1 | 10/2004 | Youn-Chyuan | |
| 2005/0075642 A1 | 4/2005 | Felt et al. | |
| 2005/0192585 A1 | 9/2005 | Simmons | |
| 2005/0285355 A1 * | 12/2005 | Lin | 279/81 |
| 2006/0009796 A1 | 1/2006 | Carusillo et al. | |
| 2006/0030853 A1 | 2/2006 | Haines | |
| 2006/0217729 A1 | 9/2006 | Eskridge et al. | |
| 2006/0229624 A1 | 10/2006 | May et al. | |
| 2007/0016238 A1 * | 1/2007 | Marietta | 606/176 |
| 2007/0123893 A1 | 5/2007 | O'Donoghue | |
| 2008/0168666 A1 | 7/2008 | Zhou | |
| 2009/0326540 A1 | 12/2009 | Estes | |

FOREIGN PATENT DOCUMENTS

| | | |
|---|---|---|
| CN | 102076273 A | 5/2011 |
| DE | 202008000255 U1 | 5/2008 |
| EP | 0056266 A1 | 7/1982 |
| EP | 2303145 A2 | 4/2011 |
| FR | 2837886 A1 | 10/2003 |
| JP | 2011526804 A | 10/2011 |
| WO | WO-2010002527 A2 | 1/2010 |

OTHER PUBLICATIONS

International Search Report mailed Dec. 16, 2009 for PCT/US/2009/045486 claiming benefit of U.S. Appl. No. 12/165,305 filed Jun. 30, 2008.

International Preliminary Report on Patentability and Written Opinion mailed Jan. 13. 2011 for PCT/US/2009/045486 claiming benefit of U.S. Appl. No. 12/165,305, filed Jun. 30, 2008.

* cited by examiner

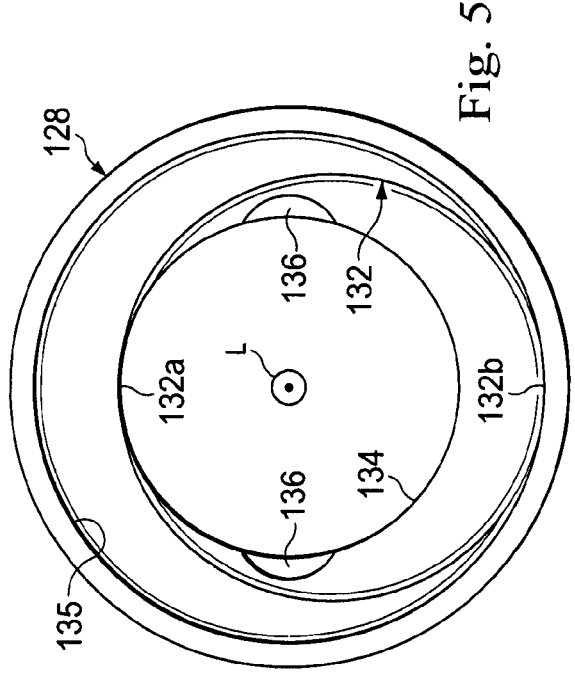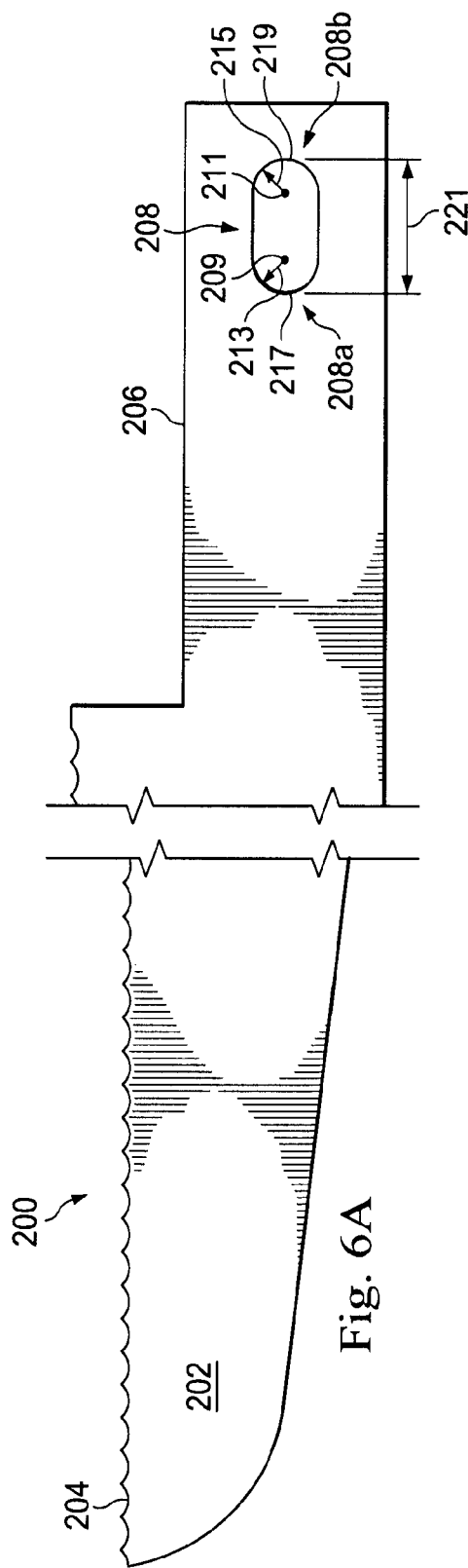

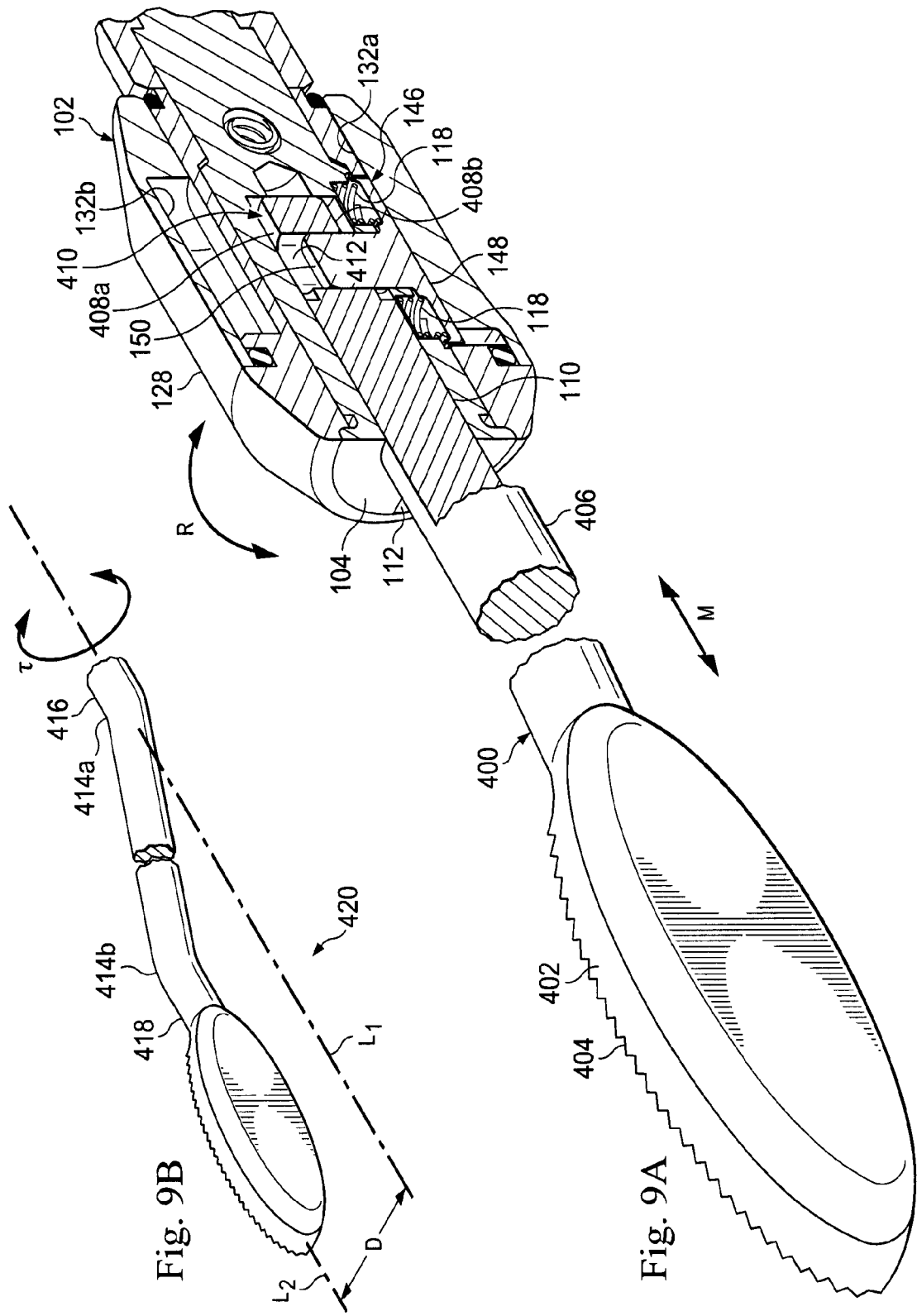

US 8,465,492 B2

CHUCK FOR RECIPROCATING SURGICAL INSTRUMENT

FIELD OF THE INVENTION

The present invention relates generally to reciprocating surgical instruments used for cutting and modifying bone or other tough tissues. In particular, the present invention relates to a chuck or collet for use with said instruments, and especially for securing various blades and other tools to said instruments.

BACKGROUND

Doctors and other medical professionals often use powered surgical instruments for dissecting bones, tissues and other purposes. Reciprocating saw-type cutting instruments may be used for surgical operations to cut through bone, cartilage, or other strong tissue. Depending on the manufacture or purpose, saw blades, bone burs, rasps, chisels, and other tools are often designed with varying tool profiles, such as flat or round shank profiles. It would be an improvement to have a reciprocating motion surgical instrument with a chuck that can readily accept blades, and other tools, having flat, round, or other shank profiles.

SUMMARY

The present invention provides improved methods and devices for securing a surgical tool, such as a cutting blade within a reciprocating surgical instrument, such as a reciprocating saw. Cutting blades and other surgical tools are described that are provided with flat, round, or other shank profiles.

According to one exemplary embodiment, a chuck is disclosed for securing a surgical tool having a shank with a securing aperture within a reciprocating motion surgical instrument. The chuck comprises a shaft and a securing member. The shaft defines an axis and has a receptacle for receiving the shank of the tool. The securing member is carried by the shaft and is selectively moveable between a first position wherein the member is substantially withdrawn from the receptacle to permit the insertion and removal of the surgical tool, and a second position wherein the member is substantially located within the receptacle and through the securing aperture to secure the surgical tool within the receptacle.

In another aspect, a securing chuck is disclosed for securing a surgical tool to a reciprocating surgical instrument that comprises a shaft and a securing member. The shaft defines an axis and has a cylindrical bore extending along the axis. The bore is shaped to receive a substantially rounded tool shank. A pair of transverse slots extends into the shaft along a plane passing through the axis for receiving a substantially flattened tool shank. The transverse slots intersect with the cylindrical bore. The securing member is carried by the shaft and is radially movable relative to the bore both inwardly and outwardly to secure the surgical tool in the chuck.

In some embodiments, a reciprocating surgical instrument comprises a motor, a transmission, a surgical tool chuck, and a surgical tool. The motor has a rotatable spindle and a transmission is mounted to the spindle for converting rotating movement of the spindle to reciprocating movement. The surgical tool chuck is coupled to the transmission and comprises a receiving shaft, a locking member, and a camming sleeve. The receiving shaft defines an longitudinal axis and has a tool receptacle and a radially extending proximal opening. The locking member is slidingly coupled to the receiving shaft and has a protrusion extending therefrom. The camming sleeve is rotatingly retained on the shaft and has an internally cammed surface. The surgical tool has a distal end and a proximal end, the proximal end configured to be received into the tool receptacle. The surgical tool has an aperture disposed to correspond with the radially extending proximal opening of the receiving shaft when the surgical tool is disposed in the attachment receptacle. The locking member is selectively moveable between a first position and a second position. In the first position the protrusion is withdrawn from the proximal opening of the receiving shaft to allow insertion and removal of the surgical tool. In the second position the protrusion is substantially received within the proximal opening of the receiving shaft and the aperture in the surgical tool to secure the surgical tool within the chuck. The cammed surface is configured to urge the protrusion into the second position.

It should be understood that the present summary and the following detailed description, while discussing some exemplary embodiments of the invention, are intended for purposes of illustration only and are not intended to limit the scope of the invention beyond that described in the claims.

BRIEF DESCRIPTION OF THE DRAWINGS

The present disclosure will become more fully understood from the detailed description and the accompanying drawings, wherein:

FIG. 5 is a an end view of a portion of the chuck of FIG. 2.

FIG. 6A is a top view of an exemplary blade for use with the chuck of FIG. 2.

FIG. 9A depicts an exemplary rasp tool having a rounded shank installed in the chuck of FIG. 2.

FIG. 9B depicts an exemplary rasp tool having an angled shank.

DETAILED DESCRIPTION

Figure 1A:
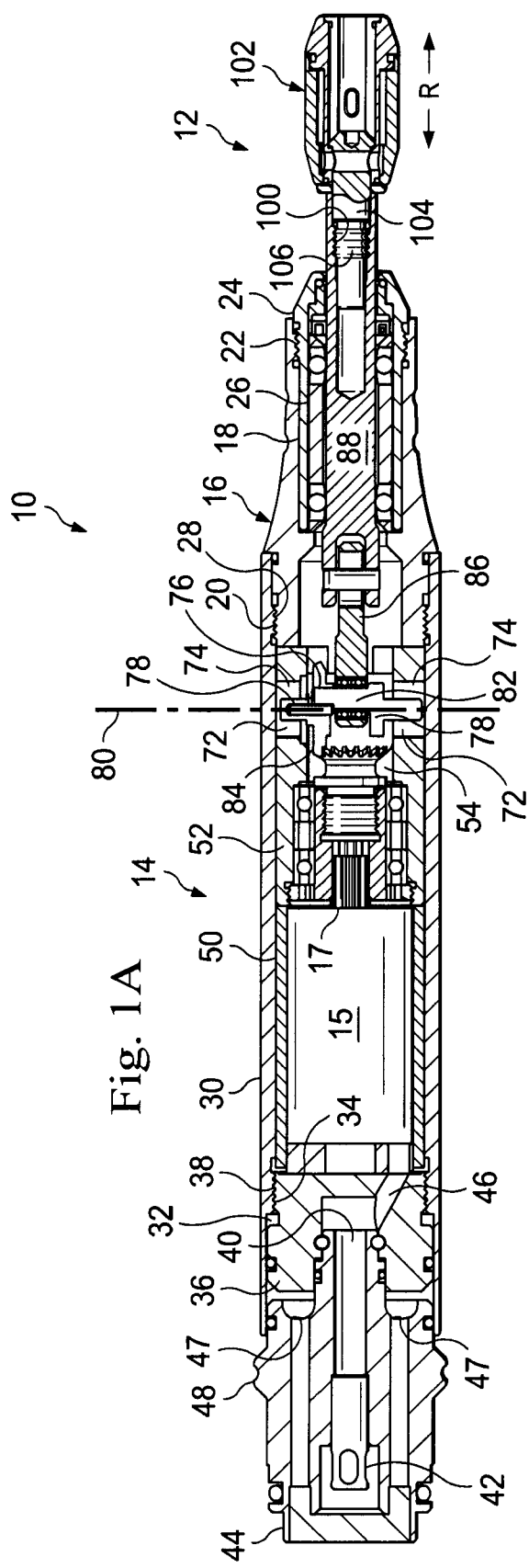
FIG. 1A is a cutaway, cross-sectional view of an exemplary reciprocating motion surgical instrument constructed in accordance with the present invention.

For the purposes of promoting an understanding of the principles of the invention, references will now be made to the embodiments, or examples, illustrated in the drawings and specific languages will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. Further, it will be understood that the present disclosure is not limited to any particular surgical application but has utility for various applications in which it is desired, including but not limited to:

1. Arthroscopy—Orthopedic
2. Endoscopic—Gastroenterology, Urology, Soft Tissue
3. Neurosurgery—Cranial, Spine, and Otology
4. Small Bone—Orthopedic, Oral-Maxiofacial, Ortho-Spine, and Otology
5. Cardio Thoracic—Small Bone Sub-Segment
6. Large Bone—Total Joint and Trauma
7. Dental and other applications Certain details of the construction of the instrument will be understood by those of skill in the art and, therefore, are not described in detail here.

Figure 1B:
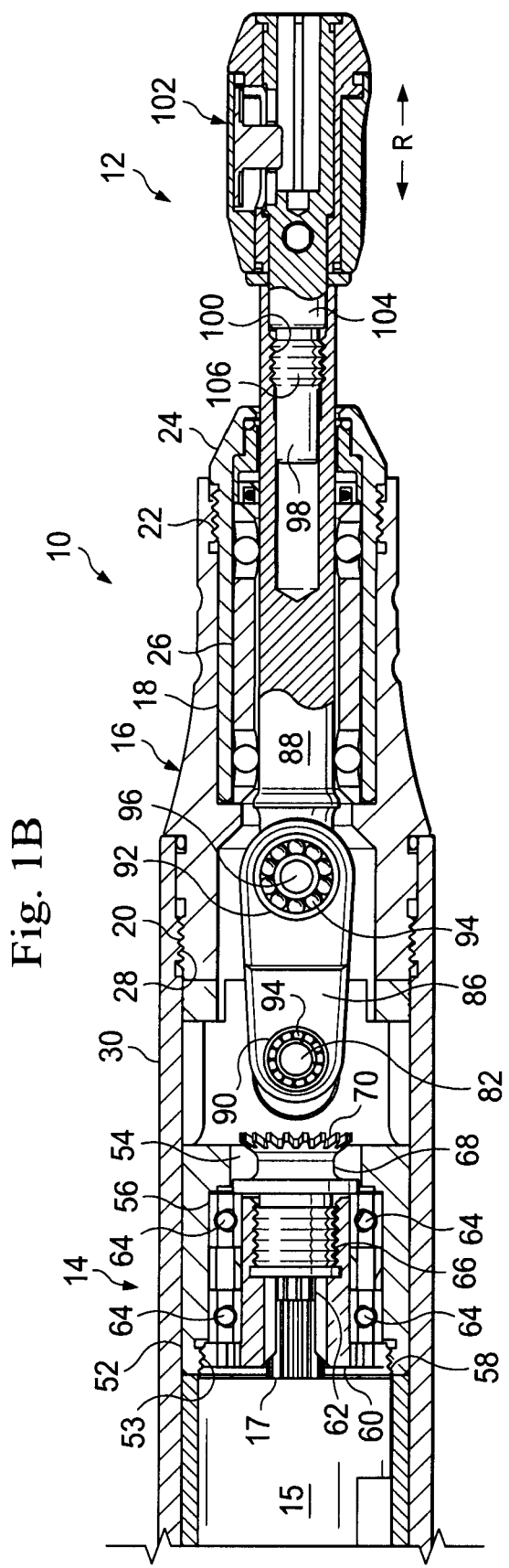
FIG. 1B is another cutaway, cross-sectional view of the exemplary reciprocating motion surgical instrument of FIG. 1A.

Referring generally to FIGS. 1A and 1B, two cutaway, cross-sectional views of an exemplary reciprocating motion surgical instrument 10 are shown. Instrument 10 has a distal working portion 12 adapted to hold a cutting blade, or other surgical tool or attachment, and a proximal driver portion 14 containing a motor 15 for operating working portion 12. Motor 15 has a splined spindle 17 on its forward, or distal, end that is rotated by motor 15.

Driver portion 14 is partially enclosed by a tapered nose piece 16 that defines a longitudinal bore 18 and has exterior threads 20 at its rear, or proximal, end and interior threads 22 at its forward, or distal, end. Interior threads 22 secure a cap 24 within the length of bore 18 of the nose piece, cap 24 providing a chamber 26 therein. Exterior threads 20 of nose piece 16 are secured to mating interior threads 28 on motor housing 30.

As can be seen from FIG. 1A, motor housing 30 provides a rearward receptacle 32 with an interiorly threaded portion 34. A coupling assembly 36 resides within receptacle 32 and has exterior threads 38 which mate with threads 34 of motor housing 30 to secure the two components together. Coupling assembly 36 has a central fluid passage 40 that extends longitudinally through assembly 36. It is noted that coupling assembly 36 is interconnected with a fluid pressure source (not shown), typically by a coaxial hose or conduit, that provides pressurized fluid (e.g., air) into the fluid passage 40. Radially interior and radially exterior slip-on fittings 42 and 44, respectively, form a seal with the coaxial hose, in a manner known in the art.

Pressurized fluid is directed from central passage 40 through an angled conduit 46 to drive motor 15. Exhaust fluid is communicated from motor 15 back to the coaxial hose through radially disposed fluid exhaust passages 47 in coupling assembly 36.

Coupling assembly 36 presents a radially expanded outer portion 48 that is shaped to provide either a knurled surface or wrench flats so that coupling assembly 36 can be more easily rotated when being affixed or removed from receptacle 32 of motor housing 30.

Referring to FIG. 1B, a motor sleeve 50 surrounds motor 15 and is contained within motor housing 30. Motor sleeve 50 is positioned forward, or distally, of coupling assembly 36 and abuts a gear housing 52 that is generally cylindrical in shape. Gear housing 52 has a central longitudinal bore 54 of reduced diameter and an enlarged diameter longitudinal bore 56 at its rear, or proximal, end. The rear portion of enlarged diameter bore 56 is interiorly threaded at 58.

Enlarged diameter bore 56 houses a gear coupling 60 that defines a splined longitudinal passage 62 therein that is adapted to surround and engage the splines of motor spindle 17 in a complimentary fashion. A pair of annular bearings 64 are disposed between gear coupling 60 and bore 56 to aid in rotation of gear coupling 60.

The distal portion of passage 62 is threaded, as shown at 66. A pinion gear 68 is secured within threaded portion 66 and provides a set of angled rotary teeth 70 at its forward end. It will be seen that when motor 15 is activated, the set of teeth 70 is rotated by the motor 15.

As shown in FIG. 1A, a pair of lateral bores 72 are cut into gear housing 52 in diametrically opposite locations, and each of the bores 72 houses an annular bearing 74. An eccentric crank 76 is maintained within longitudinal bore 54 and provides bearing pins 78 that extend outward through bearings 74 so that pins 78 can rotate within bearings 74 about their own pin axis 80. Eccentric crank 76 has a central spanning portion 82 that is offset from pin axis 80 so that it revolves about pin axis 80 when bearing pins 78 are rotated inside their bearings 74. Eccentric crank 76 also provides a pinion gear portion 84 having angled teeth that intermesh with teeth 70 of pinion gear 68. When pinion gear 68 is rotated by motor 15, teeth 70 of gear 68 engage the teeth of pinion gear portion 84 so that eccentric crank 76 is rotated by its bearing pins 78 within bearings 74. As crank 76 is rotated in this manner, spanning portion 82 is rotated about pin axis 80.

As best shown in FIG. 1B, a connecting rod 86 contained within bore 26 interconnects spanning portion 82 of eccentric crank 76 to a reciprocating shaft 88. Connecting rod 86 has a proximal opening 90 and a distal opening 92. Both openings 90 and 92 contain annular bearings 94. Spanning portion 82 passes through proximal opening 90 and bearing 94. Distal opening 92 and bearing 94 surround a pin 96 within reciprocating shaft 88. It is noted that the reciprocating shaft 88 is disposed substantially within chamber 26 of cap 24 and within bore 18 of nose piece 16. It will be understood, then, that the components described herein provide a transmission that converts rotating movement of motor spindle 17 into reciprocating movement for shaft 88 and related components. A number of bearings and sleeves, which will not be described in detail here, ensure that reciprocating shaft 88 is capable of reciprocating movement within cap 24 and nose piece 16.

The distal end of reciprocating shaft 88 extends outward beyond the distal end of cap 24, and contains a blind bore 98 that is formed therein. Blind bore 98 has an inner threaded portion 100 along its length whereby reciprocating shaft 88 can be connected to working portion 12 of instrument 10.

While instrument 10 has been described as having a pneumatic motor, it is contemplated that working portion 12 and the necessary transmission components may be similarly driven by an electric motor and handpiece. One exemplary electric handpiece is the Midas Rex® Legend EHS Stylus™ owned by Medtronic Xomed, Inc. Thus, an electric motor may provide a rotational force that the transmission converts into reciprocating movement for reciprocating shaft 88.

Figure 2:
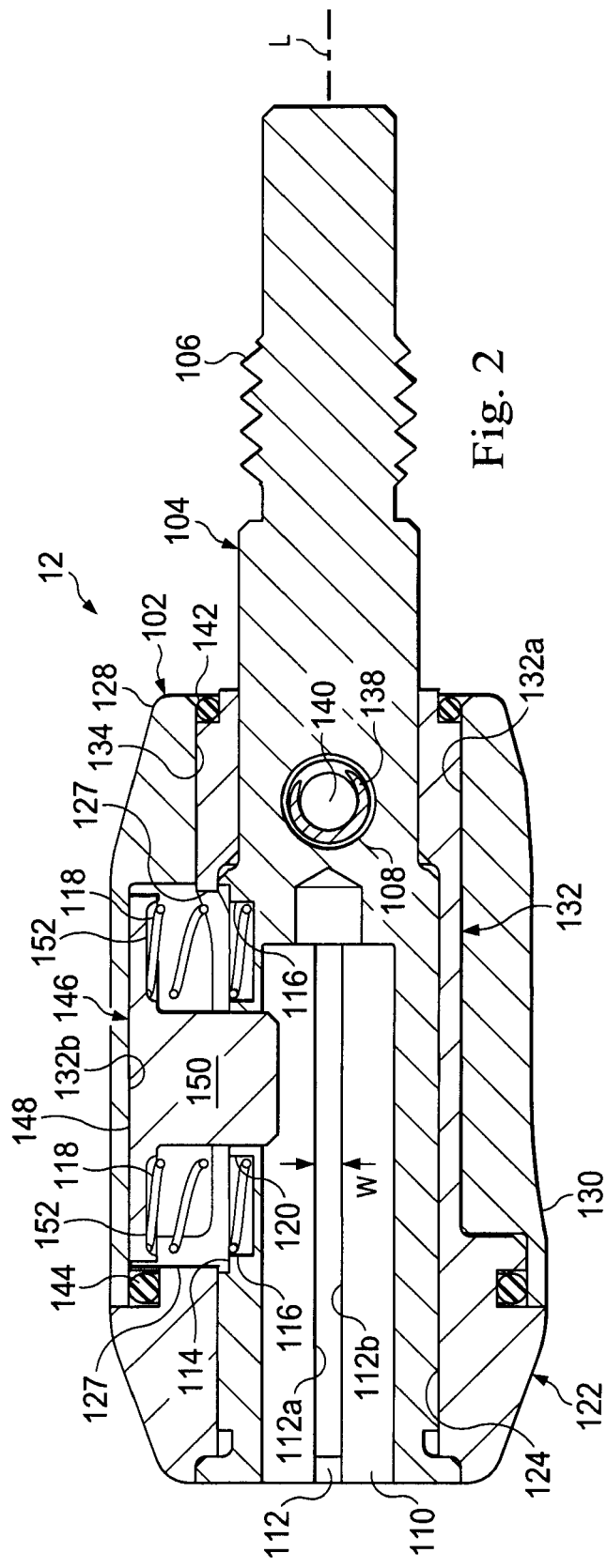
FIG. 2 is an enlarged cutaway, cross-sectional view of an exemplary chuck for use with the surgical instrument of FIGS. 1A and 1B.

Working portion 12 of instrument 10 is more easily understood with further reference to FIGS. 2-6, wherein a chuck and other components of working portion 12 are shown in greater detail. FIG. 2 is an enlarged cutaway, cross-sectional view of an exemplary collet, or securing chuck 102 for use with instrument 10. Securing chuck 102, according one exemplary embodiment, comprises a securing shaft 104 which carries external threads 106 near its proximal end. Threads 106 are shaped and sized to interconnect with the threads 100 of blind bore 98 in reciprocating shaft 88 (shown in FIG. 1B). In other embodiments, securing shaft 104 and reciprocating shaft 88 are integral, or a monolith. In yet other embodiments, the transmission may be integral with chuck 102.

Figure 3:
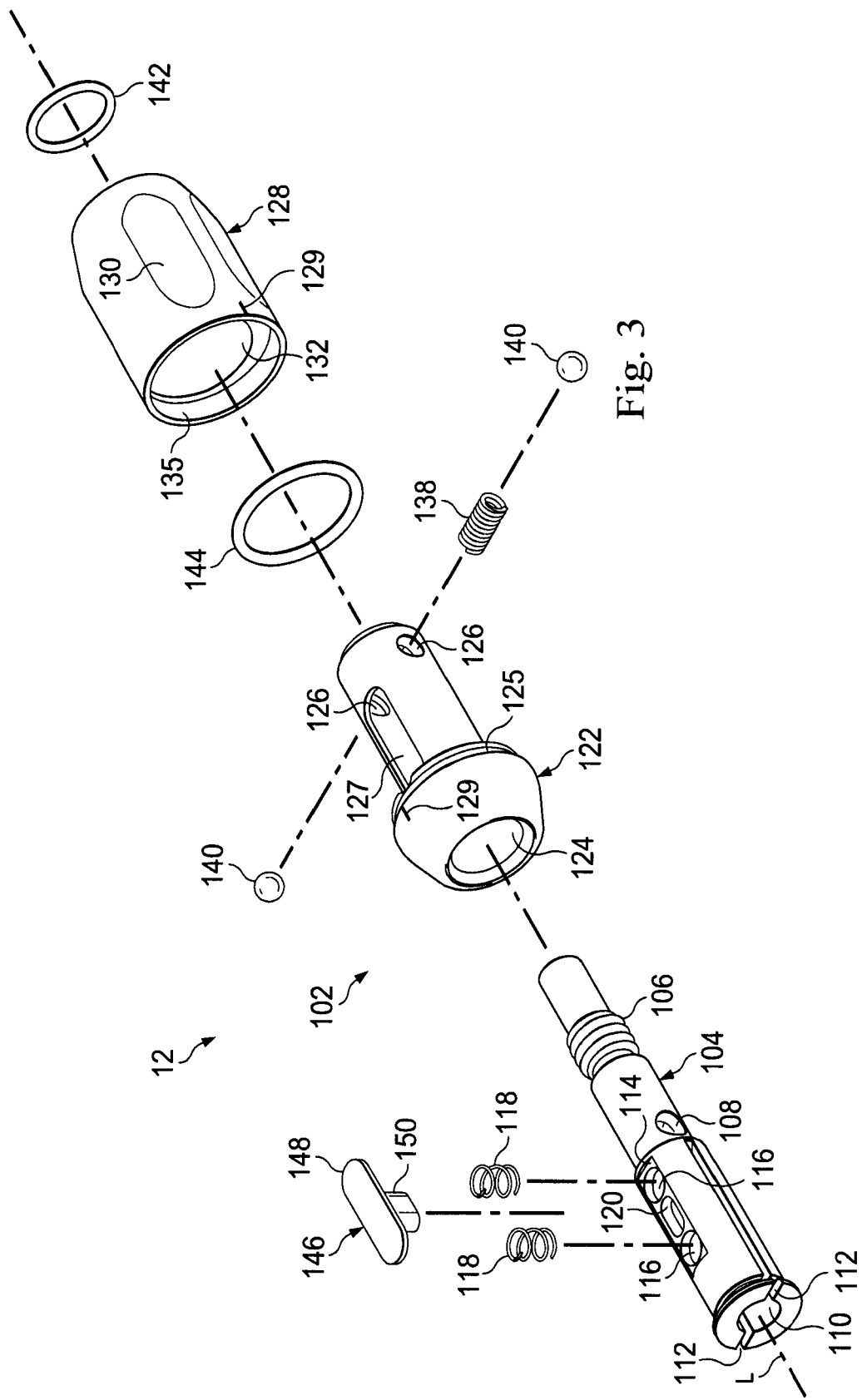
FIG. 3 is an exploded view of the chuck depicted in FIG. 2.
Figure 4:
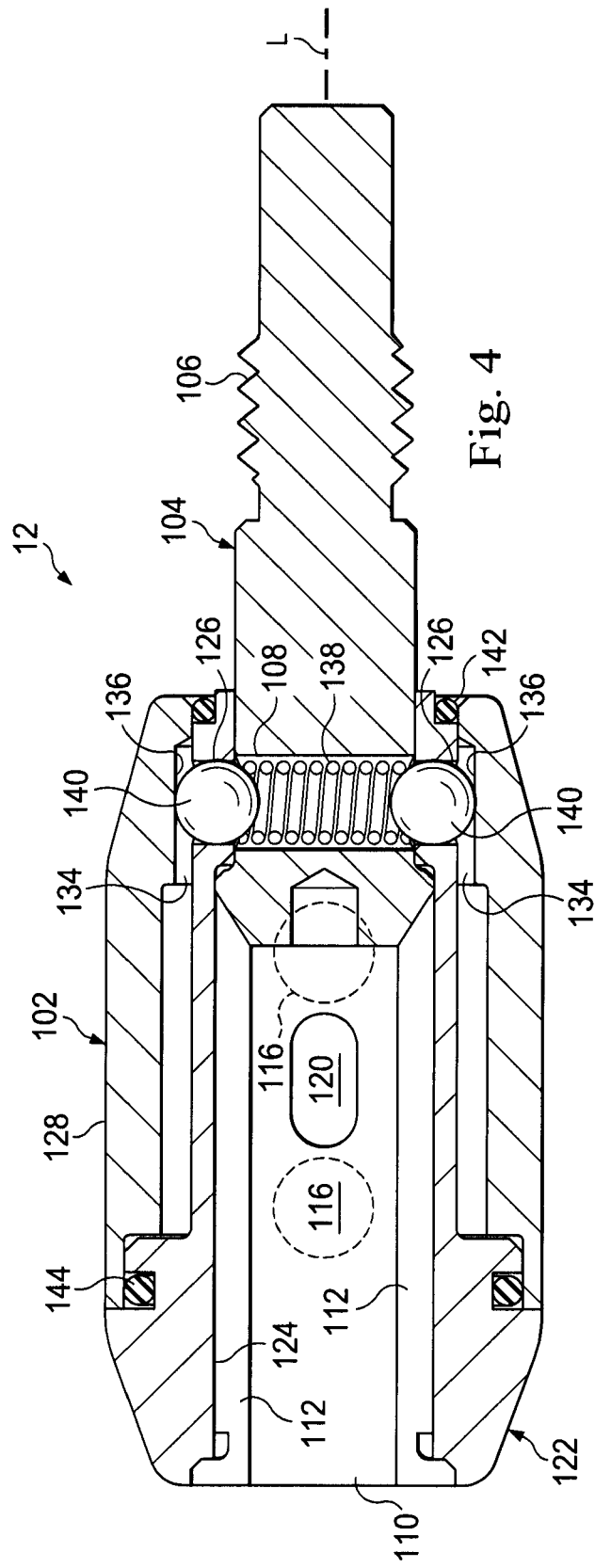
FIG. 4 is a another enlarged cutaway, cross-sectional view of the exemplary chuck in FIG. 2.

Referring now to FIGS. 3 and 4, FIG. 3 is an exploded view of the chuck 102 and FIG. 4 is a cross-sectional view of chuck 102. Shaft 104 has a lateral hole 108 laterally extending through its diameter. The distal end of securing shaft 104 contains a substantially-rounded receiving bore 110 that is centrally located within shaft 104 and aligned along a longitudinal axis L. A pair of slots 112 extend radially outward from bore 110 and are located diametrically across from one another.

Still referring to FIGS. 2 and 3, shaft 104 also has an exterior indentation 114 along one side (best shown in FIG. 3). A pair of spring retaining slots 116 are formed within the indentation 114 to provide receiving elements in shaft 104 within which springs 118 may rest. A key-hole 120 is cut through indentation 114.

As best shown in FIG. 3, a retaining sleeve 122 surrounds shaft 104 and is substantially cylindrical in shape. Sleeve 122 includes a central longitudinal bore 124 within which shaft 104 resides. A pair of lateral holes 126 and a slot 127 are cut through sleeve 122. Sleeve 122 may include other features, such as a sealing member retainer groove 125.

A rotatable camming sleeve 128 surrounds shaft 104 and retaining sleeve 122 and provides outer ridged or textured gripping surface 130. FIG. 5 is an end view of camming sleeve 128. With reference to FIGS. 3 and 5, camming sleeve 128 is hollow and provides a pair of surfaces that retain camming sleeve 128 against retaining sleeve 122, and activate a shank securing member in a manner that will be described.

An interior camming surface portion 132 is presented upon the interior distal portion of camming sleeve 128. Camming surface portion 132 is eccentrically graduated as shown in FIG. 3, and more especially in FIG. 5, so that one side 132a of camming surface portion 132 is radially closer to axis L than an opposing side 132b of camming surface portion 132. As shown particularly in FIGS. 2 and 5, camming sleeve 128 also provides an interior radial contact surface portion 134 that is equally spaced about its circumference from axis L and adapted to contact the outer surface of retaining sleeve 122 so that camming sleeve 128 is retained against retaining sleeve 122 in a rotatably slidable relation. Other surfaces and surface portions are also contemplated, such as, for example, an interface surface portion 135, as shown in FIGS. 3 and 5, for coupling camming sleeve 128 to retaining sleeve 122. In addition, contact surface portion 134 may contain one or more detents, or grooves 136, as shown in FIGS. 4 and 5, which may extend at least partway around the circumference of contact surface portion 134. Grooves 136 may further extend longitudinally in a direction generally aligned with axis L.

Referring generally to FIGS. 3 and 4, when chuck 102 of the working portion 12 is assembled, a spring 138 may extend through hole 108 in shaft 104 to bias bearing balls 140 radially outward through holes 126 of retaining sleeve 122 and into milled grooves 136 (see FIG. 4). When balls 140 enter grooves 136, an audible "click" sounds to inform the user of a locked or unlocked position. The "click" may also provide the user with a tactile verification of the position as locked or unlocked. In addition, one or more external surface marks 129 may be included to visually indicate a locked or unlocked positioned, as shown in FIG. 3. For example, corresponding surface marks 129 may be included on camming sleeve 128 and retaining sleeve 122.

Spring 138, balls 140, and grooves 136 cooperate to maintain camming sleeve 128 in a locked position or in an unlocked position. In addition, spring 138, balls 140, and grooves 136 may function to keep camming sleeve 128 rotatingly retained over retaining sleeve 122. For example, a continuous circumferential lateral groove (not shown) snapped over balls 140 may keep camming sleeve 128 rotatingly retained over retaining sleeve 122. Balls 140 may further assist in supporting camming sleeve 128 as it is rotated. Spring 138 may further function to help retain shaft 104 inside retaining sleeve 122.

Rubber o-rings 142 and 144 may be used to assist in creating a fluid-tight seal between the components, and which may be retained by features such as groove 125, as shown in FIG. 3, and discussed above.

Referring now to FIGS. 2 and 3, a securing member, such as key pin 146, may include an enlarged contact head 148 and a radially inward-extending protrusion, key portion 150. Key portion 150 may be shaped and sized to reside within a complimentary-shaped aperture in securing shaft 104, as will be described. Contact head 148 resides generally within slot 127 of retaining sleeve 122. Key portion 150 extends radially inward through key-hole 120 of milled-away portion 114 of shaft 104 and into bore 110. Springs 118, residing within spring retaining slots 116, contact seating surfaces 152 (see FIG. 2) on the underside of contact head 148 to bias securing member 146 radially outward. When chuck 102 of the working portion 12 is assembled, camming surface portion 132 contacts the outer radial side of contact head 148.

Figures 6B, 7A:
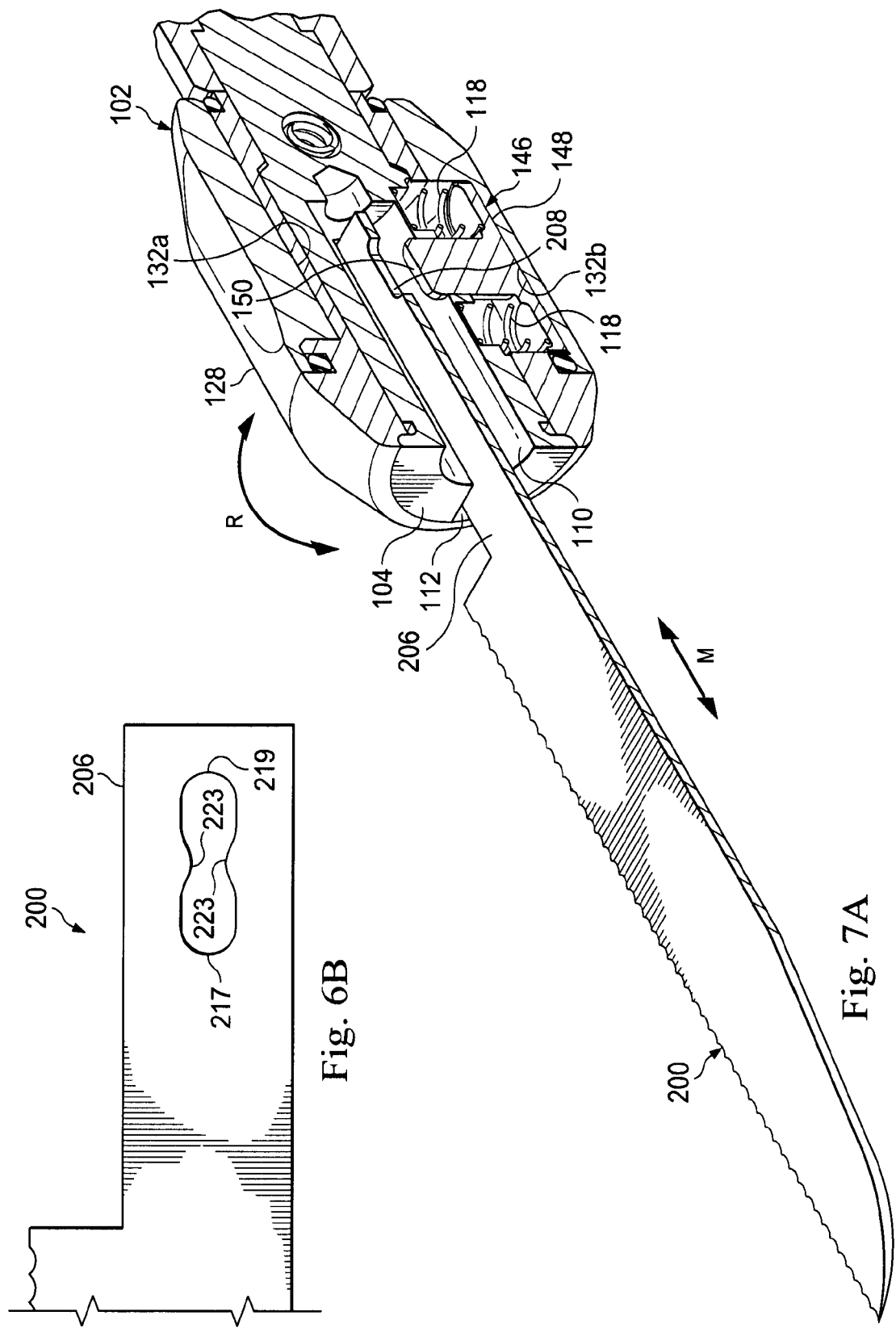
FIG. 6B is a top view of another exemplary blade for use with the chuck of FIG. 2.
FIG. 7A is a cutaway, cross-sectional view of the blade of FIG. 6A installed in the chuck of FIG. 2.

Referring now to FIGS. 6A and 6B, top views of two exemplary flat-shanked cutting blades for use with chuck 102 are shown. Beginning with FIG. 6A, blade 200 has a cutting portion 202 with a serrated edge 204. It will be understood that other cutting shapes and structures may be used for cutting portion 202.

Blade 200 has a flattened shank 206 having an aperture 208 cut therethrough. Aperture 208 is substantially sized to be complimentary to key portion 150 of securing member 146. Aperture 208 has two ends 208a and 208b that, in the example shown, are each substantially circular in shape and, here, are identical in shape. According to one embodiment, each end 208a and 208b may have a center point 209 and 211 and circumferences 217 and 219. Radiuses 213 and 215 extend from center points 209 and 211, respectively. Ends 208a and 208b are spaced apart from one another by an offset distance 221. Thus, the distance between center points 209 and 211, is greater than the sum of radiuses 213 and 215 (see FIG. 6A).

As shown in FIG. 6B, a pair of inwardly directed ridges 223 may be provided between circumferences 217 and 219, and which exclude portions of non-complimentary key portions. In one exemplary embodiment, the shank aperture and key portion have complimentary profiles which resemble an hourglass. In some embodiments, the shank aperture and key portion have a shape that is square, rectangular, dumbbell shaped, circular, scalloped, among others. In other embodiments, the profiles are non-symmetrical and may include a lateral bias such that the blade may be securable in only one orientation. For example, the aperture and key portion may be located lateral from axis L such that the aperture is an open notch in a side of the shank, rather than an enclosed aperture. In yet other embodiments, more than one aperture and more than one key portion permit secure and consistent blade alignment.

The shape of aperture 208 ensures that only a key having a substantially complimentary shape can be disposed within the aperture. Thus, the chance of blade 200 being used with an incompatible device having a non-complimentary key portion is reduced.

Figure 7B:
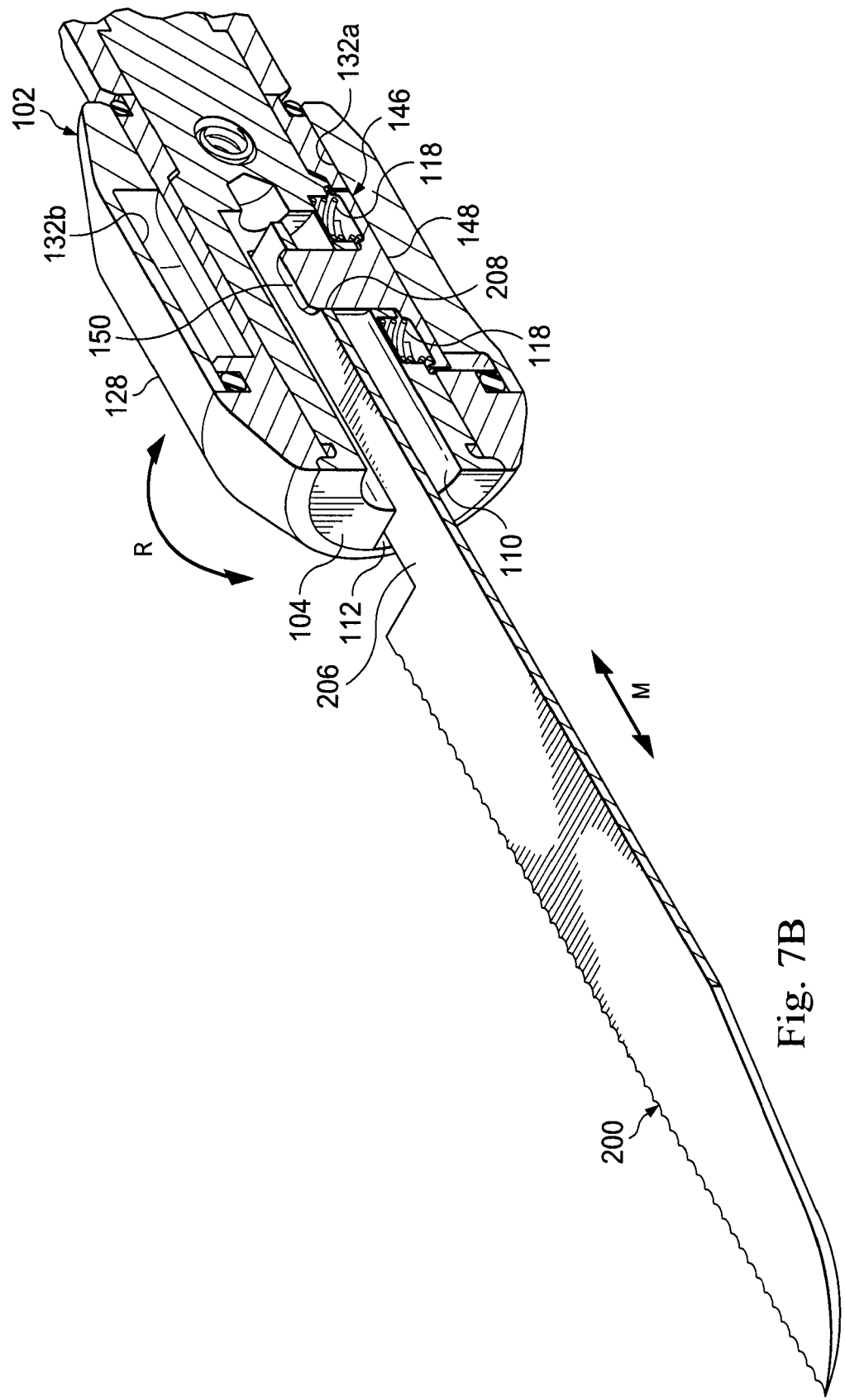
FIG. 7B is another cutaway, cross-sectional view of the blade of FIG. 6A installed in the chuck of FIG. 2.

Referring now to FIGS. 7A and 7B, cross-sectional views of blade 200 are depicted installed in chuck 102. Beginning with FIG. 7A, blade 200 is secured within the chuck 102 by inserting shank 206 inside bore 110 so that flat shank 206 is retained within slots 112. Flat shank 206 has a width dimension greater than the diameter of central bore 110, and therefore extends into, and is received within, slots 112.

Prior to insertion, camming sleeve 128 should be rotated in a direction indicated by rotation arrows R substantially to the position shown in FIG. 7A. In this first position, radially enlarged portion 132b of camming surface portion 132 is adjacent contact head 148 of securing member 146, thereby permitting springs 118 to bias securing member 146 radially outward.

Turning now to FIG. 7B, camming sleeve 128 is then rotated so that radially reduced portion 132a is located adjacent contact head 148. In this second position, securing member 146 is urged radially inward, which compresses springs 118 and translates key portion 150 into blade aperture 208, thereby securing blade 200 within chuck 102.

In one embodiment, chuck 102 is configured such that cam sleeve 128 may be rotated through 180 degrees to completely translate the key portion between the first position and the second position. In other embodiments, chuck 102 is configured such that cam sleeve 128 may be rotated more or less than 180 degrees to translate the key portion between the first second positions. In one embodiment, chuck 102 is configured for 90 degree rotation.

In one embodiment, cam sleeve 128 may be configured to be rotated perpetually in either the clockwise or counter-clockwise directions. Such perpetual rotatability may increase the ease of use for an operator. In other embodiments, one or more stops may be included so that rotation between the first and second positions is limited to rotation between the one or more stops.

In order to remove or replace a blade, or other tool within chuck 102, the operations described here are essentially reversed. Camming sleeve 128 is rotated so that radially enlarged portion 132b of camming surface portion 132 is positioned adjacent contact head 148, thereby permitting the securing member 146 to be urged radially outward by springs 118 so that key portion 150 is removed from aperture 208. Blade 200 can then be withdrawn from slots 112 and chuck 102.

As noted above, the securing, or locking of blade 200 is accomplished without compressing or reducing a compressible collet against the blade. Thus, according to one embodiment, chuck 102 is a key-less chuck since a surgical tool may be securely attached to chuck 102 without wrenches, chuck keys, and the like. Neither is it required to tighten and loosen threads by hand, which threads may bind leading to delay in tool change-over.

In addition, slots 112 have upper and lower opposing inner surfaces 112a and 112b, as shown in FIG. 2. Opposing inner surfaces 112a and 112b are spaced apart by a slot width W that is substantially equal at all points between surfaces 112a and 112b. Thus, slot width W is substantially maintained at the same width whether the tool is secured or unsecured in the chuck.

Figure 8:
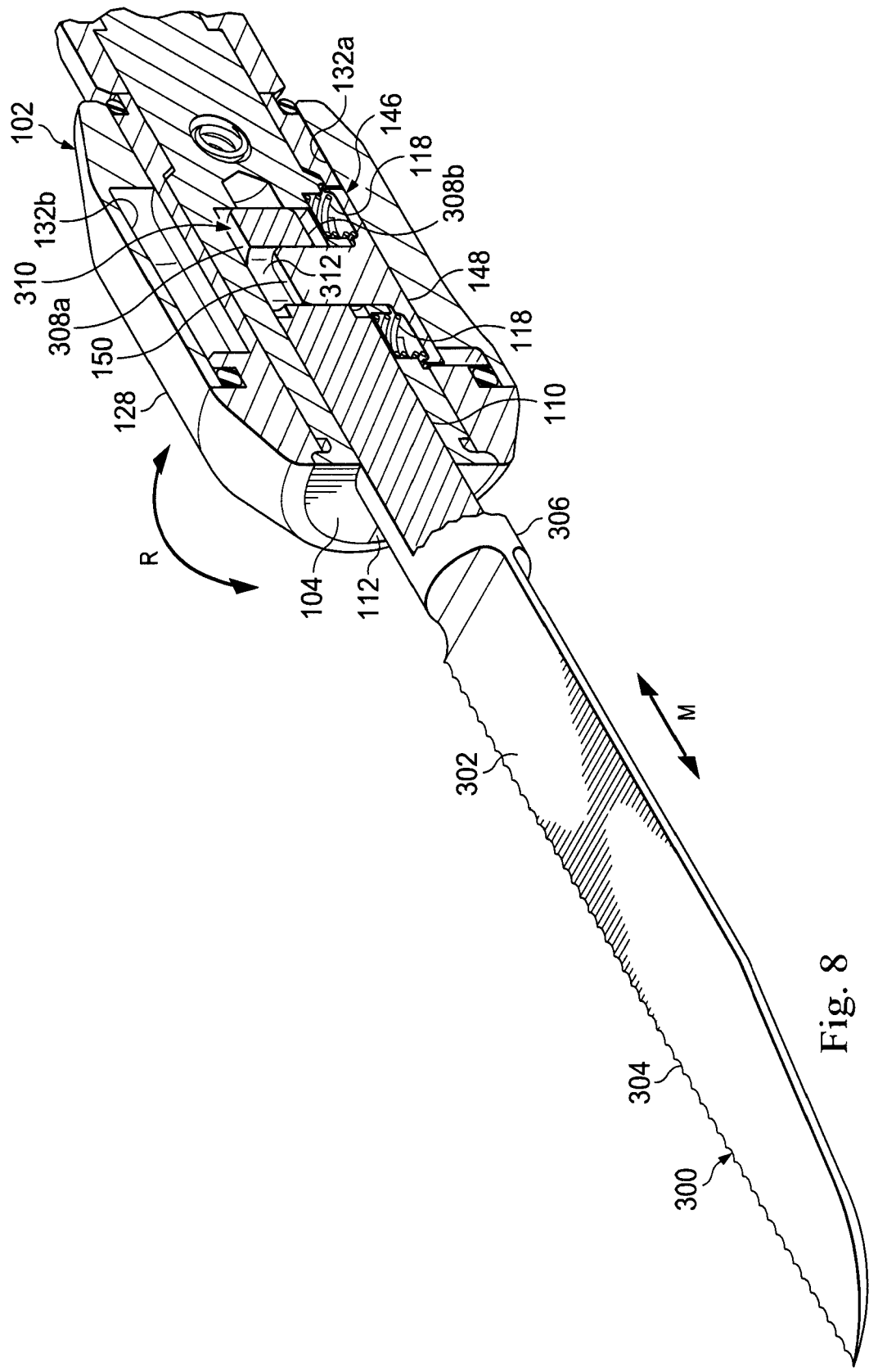
FIG. 8 depicts an exemplary cutting blade having a rounded shank installed in the chuck of FIG. 2.

Referring now to FIG. 8, an exemplary cutting blade 300 having a rounded shank is depicted. Blade 300 has a cutting portion 302 with serrated edge 304 that may be similar in configuration to cutting portion 202 and edge 204 described earlier. Blade 300 has a rounded shank 306 which may have a pair of upper and lower cutaway portions 308a and 308b, respectively, at the proximal end of shank 306. Upper and lower cutaway portions 308a and 308b define a flattened section 310. An aperture 312, which may be shaped and sized similar to aperture 208 described earlier, is disposed in flattened section 310.

Thus, rounded shank 306 may have a first diameter, or first height, sized to substantially fill cylindrical bore 110, and a second diameter, or second height less than the first height. The second height corresponds to the reduced thickness of flattened section 310 after portions 308a and 308b are cutaway. In other embodiments, only one side of rounded shank 306 is cutaway. This reduction in height provides a unique advantage, such that key protrusion 150 does not have to travel as far to enter and exit the shank aperture. Thus, the travel distance of key protrusion 150 between the first and second positions is reduced, allowing for a reduction in the maximum thickness of camming sleeve 128. Hence, the overall profile of chuck 102 may be reduced to provide better access, safety, and other benefits.

An additional benefit yielding from the reduced overall profile relates to the mass of the chuck. The rapid, repetitive direction change inherent to reciprocating motion is encumbered as more and more mass is added and made to quickly change direction. Thus, by reducing the mass profile of the chuck, the motor, transmission, and dampening features may all benefit from decreased wear, vibration, and power loss. In addition, the size and weight of the handpiece may be further reduced due to the reduced loading. A reduction in weight and vibration, along with improved balance may increase user accuracy and reduce user fatigue during surgical procedures.

In other embodiments rounded shank 306 has no cutaways but extends its entire length at the first diameter.

Bore 110 and slots 112 of shaft 104 provide a receptacle that is capable of receiving surgical tools having a substantially rounded shank cross-section, such as blade 300, or a substantially flattened flat cross-section, such as blade 200. Rounded shank 306 is sized and shaped to be retained within bore 110 of shaft 104. Thus, rounded shank blade 300 is inserted into bore 110 in substantially the same manner as blade 200, however, no portion of shank 306 will be disposed within slots 112 of shaft 104. Blade 300 is similarly secured within chuck 102 by rotating camming sleeve 128 to bias securing member 146 radially inward so that key portion 150 passes through aperture 312 of shank 306. Blade 300 is also removed from chuck 102 in the same manner as blade 200.

Referring now to FIG. 9A, an exemplary rasp tool having a rounded shank is depicted. Rasp tool 400 has a working portion 402 with rasp surface 404 Rasp tool 400 has a rounded shank 406 which may have a pair of upper and lower cutaway portions 408a and 408b, respectively, at a proximal end of shank 406. Upper and lower cutaway portions 408a and 408b define a flattened section 410. An aperture 412, which is shaped and sized similar to aperture 208 described earlier, is disposed in flattened section 410.

According to one exemplary embodiment shown in FIG. 9B, a rasp tool 420, usable in place of rasp tool 400, may include a rounded shank with pre-configured bends or contours, such as offset bends 414a and 414b. Thus, a proximal shank portion 416 is generally aligned with a first longitudinal axis $L_1$, and a distal shank portion 418 is generally aligned with second longitudinal axis $L_2$. Axis $L_1$ is generally offset from axis $L_2$ by an offset distance D. An offset shank may be configured to promote access and visibility, though other shank configurations are contemplated, such as a shank with a single 90 degree bend transverse to axis $L_1$, for example.

In some applications, it may be preferable to have a round-shanked surgical tool because the column strength is greater at extended distances. For example, a long-reach flat-shanked blade may be more prone to buckling than a similarly extended round-shanked blade. Other applications, not requiring an extended reach, may require the thin kerf and cutting efficiency of a flat-shanked blade. Thus, the novel chuck disclosed offers an advantage to users who may now easily change between round- and flat-shanked tools without wrenches, special chuck keys, and the like.

In addition, procedures involving increased pressures, or alternating tool force directions—such as may prevail in a rasping application—may benefit from a round shank. A rasping tool may include a head that has more mass than a saw blade, such that increased pull-out forces act on the shank during the reciprocating instrument's upstroke. In such a situation, the present disclosure may offer an advantage over a friction locking collet, such as a split jaw collet, by providing a physical interference locking protrusion extending through the shank aperture that may resist such forces. In addition, locking protrusion 150 may prevent axial rotation of a rounded shank, especially axial rotation of an offset rounded shank, as shown in FIG. 9B. Working pressure applied to working portion 402 may be magnified by offset distance D to create a rotational moment introducing torque T about axis $L_1$. Undesired axial rotation during a surgical procedure could be detrimental. However, according to this embodiment, locking protrusion 150 structurally impedes rotational motion due to the torque T to keep rasp tool 400 from spinning within the collet. Although the offset shank is shown on a rasp tool, it is understood that the offset shank may be used with any tool, including for example, saw blades, chisels, burs, and others.

In one embodiment a rounded shank may include one or more lateral extensions which are longitudinally aligned but project radially outwardly from the outer surface of the shank. The lateral extensions may extend into existing slots 112 or into additional slots or key-ways, and may resemble, at least partially, the edges of a flat shank. In other embodiments, the lateral extensions may be bosses, or they may be formed from key-stock, for example.

It is further noted that in the embodiment shown, the chuck is a key-less chuck. Accordingly, the chuck is configured to lock and unlock the tool without requiring a chuck key or other tool component to aid with controlling the chuck. Instead, the chuck may be turned by hand, and may include flats or slight recesses that aid in gripping the chuck with a user's fingers. Either a flat- or round-shank tool may have anti-rotation and anti-pullout features for securing the tool in a key-less chuck, the aperture may have a pair of side walls having a length with a width between them and distal and proximal end walls. The side wall length may be greater than the width between the side walls. Thus, an anti-rotation feature may comprise a flattened shank edge of a flat-shank blade or the sidewalls in an aperture of either type of shank. An anti-pullout feature may comprise the proximal end wall of an aperture of either type of shank.

It can be seen from the foregoing description that rotation of camming sleeve 128 about retaining sleeve 122 will move securing member 146 between a first position and a second position. In the first position, key portion 150 is not substantially withdrawn from the receptacle of shaft 104 so that a surgical tool shank may be inserted or removed therefrom. In the second position, key portion 150 is disposed substantially within the receptacle of shaft 104 so that, if a surgical tool shank is present within the receptacle, key portion 150 will be disposed through the aperture of the surgical tool shank, thereby securing the tool within chuck 102.

In operation for reciprocating motion, instrument 10 is actuated by motor 15 to move the blade, rasp, chisel, or other tool in a reciprocating manner represented by motion arrows M, as shown in FIGS. 7A-9. Motor 15 rotates pinion gear 68 which, in turn, rotates eccentric crank 76. As crank 76 is rotated, its movement reciprocates connecting rod 86 and reciprocating shaft 88, as well as chuck 102. It should be understood that other embodiments may provide reciprocating motion in other directions, such as circular or transverse directions.

In one exemplary embodiment, a round shank aperture and corresponding key portion have complimentary profiles which resemble an hourglass. In other embodiments, the profiles are non-symmetrical and may include a lateral, bias or offset such that the blade may be securable in only one orientation. For example, the aperture and key portion may be located lateral from axis L such that the aperture is an open notch in a side of the shank, rather than an enclosed aperture. In yet other embodiments, more than one aperture and more than one key portion permit secure and consistent blade alignment.

These embodiments for varying features of the apertures and corresponding key portions of either round- or flat-shank tools may provide proprietary protection. For example, an aperture configured with one of an hourglass shape, an asymmetrical shape, and a longitudinal offset may prevent non-proprietary blades from being used with the disclosed chuck. Alternatively, corresponding variations to key portion features may prevent a non-proprietary chuck from being used with the disclosed surgical tools.

While the invention has been shown in only one of its forms, it should be apparent to those skilled in the art that it is not so limited, but it is susceptible to various changes without departing from the scope of the invention.

I claim:

1. A system for treating a tissue structure during a surgical procedure, comprising:
   a reciprocating surgical instrument, comprising:
      a motor having a rotatable spindle;
      a transmission mounted to the spindle for converting rotating movement of the spindle to reciprocating movement;
      a surgical tool chuck coupled to the transmission, the chuck comprising:
         a receiving shaft defining a longitudinal axis and having a tool receptacle and a radially extending proximal opening;
         a locking member slidingly coupled to the receiving shaft, the locking member having a protrusion extending therefrom;
         a camming sleeve rotatingly retained on the shaft, the camming sleeve having first and second internal surface portions, the first surface portion having an internally cammed surface, the second surface portion having a circumference equally spaced from the axis with at least one detent formed therein;
         a rotation maintaining mechanism comprising a detent and a locking element that selectively engages the detent, the locking mechanism being at least partially disposed in the second surface portion of the camming sleeve; and
   a surgical tool having a distal end and a proximal end, the proximal end configured to be received into the tool receptacle, the surgical tool having an aperture disposed to correspond with the radially extending proximal opening of the receiving shaft when the surgical tool is disposed in the tool receptacle, wherein the locking member is selectively moveable between a first position and a second position, the first position wherein the protrusion is withdrawn from the proximal opening of the receiving shaft to allow insertion and removal of the surgical tool, the second position wherein the protrusion is substantially received within the proximal opening of the receiving shaft and the aperture in the surgical tool to secure the surgical tool within the chuck, the cammed surface configured to urge the protrusion into the second position and the rotation maintaining mechanism configured to maintain the camming sleeve in a position maintaining the protrusion in the second position.

2. The system of claim 1, further comprising a spring coupled to the shaft and disposed to bias the protrusion toward the first position.

3. The system of claim 2 wherein the locking member has a head portion with an inner surface, the protrusion extending therefrom, the head portion having a length dimension wider than the protrusion, the inner surface having at least one spring engagement feature for engaging the spring.

4. The system of claim 1 wherein the tool receptacle comprises a cylindrical bore in the shaft to receive a surgical tool with a substantially cylindrical shank.

5. The system of claim 4 wherein the surgical tool has a shank with first and second diameters, the first diameter sized to substantially fill the cylindrical bore and the second diameter representing a reduced thickness configured to reduce a travel distance of the protrusion between the first and second positions, thereby reducing an overall profile of the chuck.

6. The system of claim 1 wherein the camming surface is directed radially inward and slidingly contacts the locking member, the camming surface being radially graduated to provide a radially enlarged portion and a radially reduced portion so that the locking member is selectively moveable radially between its first and second positions as the camming sleeve is rotated about the longitudinal axis.

7. The system of claim 1 wherein rotating the camming sleeve through 180 degrees completely translates the protrusion between the first position and the second position.

8. The system of claim 4 wherein the surgical tool has an offset shank including a first portion generally aligned with the longitudinal axis and a second portion generally aligned with an offset axis, the offset axis being generally parallel to the longitudinal axis and offset from the longitudinal axis by an offset distance.

9. The system of claim 1 wherein the surgical tool chuck is key-less.

10. The system of claim 1 wherein the surgical tool has a shank, the shank having an anti-rotation feature and an anti-pullout feature for securing the tool in a key-less chuck, the aperture having a pair of side walls having a length, a width between the pair of side walls, and a proximal end wall, the side wall length being greater than the width between the pair of side walls, wherein the anti-rotation feature is at least one of a flattened shank edge and the pair of sidewalls and wherein the anti-pullout feature is the proximal end wall.

11. The system of claim 1 wherein the surgical tool aperture is one of an hourglass shape, an asymmetrical shape, and a longitudinal offset.

12. The system of claim 1 further comprising a retainer sleeve arranged between the camming sleeve and the receiving shaft, the second surface portion of the camming sleeve rotatingly engaging the retainer sleeve, the retainer sleeve having a slot which is sized to permit movement of the protrusion between the first and second positions.

13. The system of claim 12 wherein the retainer sleeve and the receiving shaft include aligned transverse holes, wherein the locking element comprises:
opposing balls slidingly arranged in aligned transverse holes of the retainer sleeve, the camming sleeve second surface portion including grooves configured to receive the balls when the camming sleeve grooves are aligned with the balls such that the camming sleeve is secured against free rotation by the balls; and
a spring biasing the balls radially outwardly.

14. The system of claim 1 wherein the detent is formed within the camming sleeve second surface portion, and wherein the locking element is retained within the receiving shaft and biased radially outward to become disposed within the detent upon rotation of the camming sleeve to a predetermined position.

15. The system of claim 14 wherein the locking element becoming disposed in the detent creates at least one of tactile feedback and audible feedback to an operator.

16. The system of claim 1 further comprising a spring coupled to the receiving shaft to bias the locking element outwards.

17. The system of claim 1 wherein the locking element comprises a ball that selectively engages the detent.

18. A system for treating a tissue structure during a surgical procedure, comprising:
a reciprocating surgical instrument, comprising:
a motor having a rotatable spindle;
a transmission mounted to the spindle for converting rotating movement of the spindle to reciprocating movement;
a surgical tool chuck coupled to the transmission, the chuck comprising:
a receiving shaft defining a longitudinal axis and having a tool receptacle and a radially extending proximal opening;
a locking member slidingly coupled to the receiving shaft, the locking member having a protrusion extending therefrom;
a camming sleeve rotatingly retained on the shaft, the camming sleeve having an internally cammed surface; and
a rotation maintaining mechanism configured to maintain the camming sleeve in a position maintaining the protrusion in a second position; and
a first surgical tool and a second surgical tool both having a distal end and a proximal end, the proximal end configured to be received into the tool receptacle, the surgical tool having an aperture disposed to correspond with the radially extending proximal opening of the receiving shaft when the surgical tool is disposed in the tool receptacle, wherein the locking member is selectively moveable between a first position and a second position, the first position wherein the protrusion is withdrawn from the proximal opening of the receiving shaft to allow insertion and removal of the surgical tool, the second position wherein the protrusion is substantially received within the proximal opening of the receiving shaft and the aperture in the surgical tool to secure the surgical tool within the chuck, the cammed surface configured to urge the protrusion into the second position;
wherein the tool receptacle comprises a cylindrical bore in the shaft to receive the first surgical tool having a substantially cylindrical shank, and
wherein the tool receptacle further comprises a transverse slot extending through opposing sidewalls of the shaft configured to receive the second surgical tool having a substantially flattened shank, where the substantially flattened shank is flattened relative to the substantially cylindrical shank.

* * * * *

UNITED STATES PATENT AND TRADEMARK OFFICE
CERTIFICATE OF CORRECTION

| | | |
|---|---|---|
| PATENT NO. | : 8,465,492 B2 | Page 1 of 1 |
| APPLICATION NO. | : 12/165305 | |
| DATED | : June 18, 2013 | |
| INVENTOR(S) | : Estes | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1420 days.

Signed and Sealed this
Sixth Day of January, 2015

Michelle K. Lee
*Deputy Director of the United States Patent and Trademark Office*